(12) United States Patent
Priatna et al.

(10) Patent No.: US 7,706,855 B1
(45) Date of Patent: Apr. 27, 2010

(54) SYSTEM AND METHOD FOR MR DATA ACQUISITION WITH UNIFORM FAT SUPPRESSION

(75) Inventors: Agus Priatna, Waukesha, WI (US);
Anthony T. Vu, Waukesha, WI (US);
Xiaoli Zhao, New Berlin, WI (US)

(73) Assignee: General Electric Company, Schenectady, NY (US)

( * ) Notice: Subject to any disclaimer, the term of this patent is extended or adjusted under 35 U.S.C. 154(b) by 1329 days.

(21) Appl. No.: 10/710,555

(22) Filed: Jul. 20, 2004

(51) Int. Cl.
*A61B 5/05* (2006.01)

(52) U.S. Cl. .................. 600/410; 600/407; 600/408; 600/409; 600/411; 600/423; 324/306; 324/307; 324/308; 324/309; 324/318; 324/319; 324/320; 324/321; 324/322; 382/128

(58) Field of Classification Search .............. 600/407, 600/408, 410–423; 324/306–309, 318–322; 382/128

See application file for complete search history.

(56) References Cited

U.S. PATENT DOCUMENTS

| | | | | |
|---|---|---|---|---|
| 6,016,057 A | * | 1/2000 | Ma | 324/309 |
| 6,373,249 B1 | * | 4/2002 | Kwok et al. | 324/306 |
| 2002/0188190 A1 | * | 12/2002 | Kassai et al. | 600/410 |
| 2005/0070785 A1 | * | 3/2005 | Ahluwalia et al. | 600/410 |
| 2005/0165294 A1 | * | 7/2005 | Weiss | 600/410 |

OTHER PUBLICATIONS

Haacke, E. Mark et al, Magnetic Resonance Imaging, 1999, John Wiley and Sons, pp. 12, 192, 429, 454-460, 516, 594, 812.*
Bellemann, M.E. et al, Drug-Specific F19 NMR and Dynamic F-18 PET Imaging of the Cytostatic Agent 5-Fluorouracil, Bellemann, M.E. et al, IEEE Transactions on Nuclear Science, vol. 41, No. 6, Dec. 1994, p. 2856.*

* cited by examiner

*Primary Examiner*—Brian Casler
*Assistant Examiner*—John F Ramirez
(74) *Attorney, Agent, or Firm*—Ziolkowski Patent Solutions Group, SC

(57) ABSTRACT

A system and method of MR imaging is disclosed that includes reconstruction of MR images with uniform or homogeneous fat suppression. An imaging process is performed using partial asymmetric acquisitions in conjunction with zero-filling of k-space for dynamic contrast-enhanced imaging. Data acquisition is carried out in a relatively short period of time which reduces scan time, reduces the likelihood of subject discomfort and motion-induced artifacts, and increases patient throughput.

25 Claims, 5 Drawing Sheets

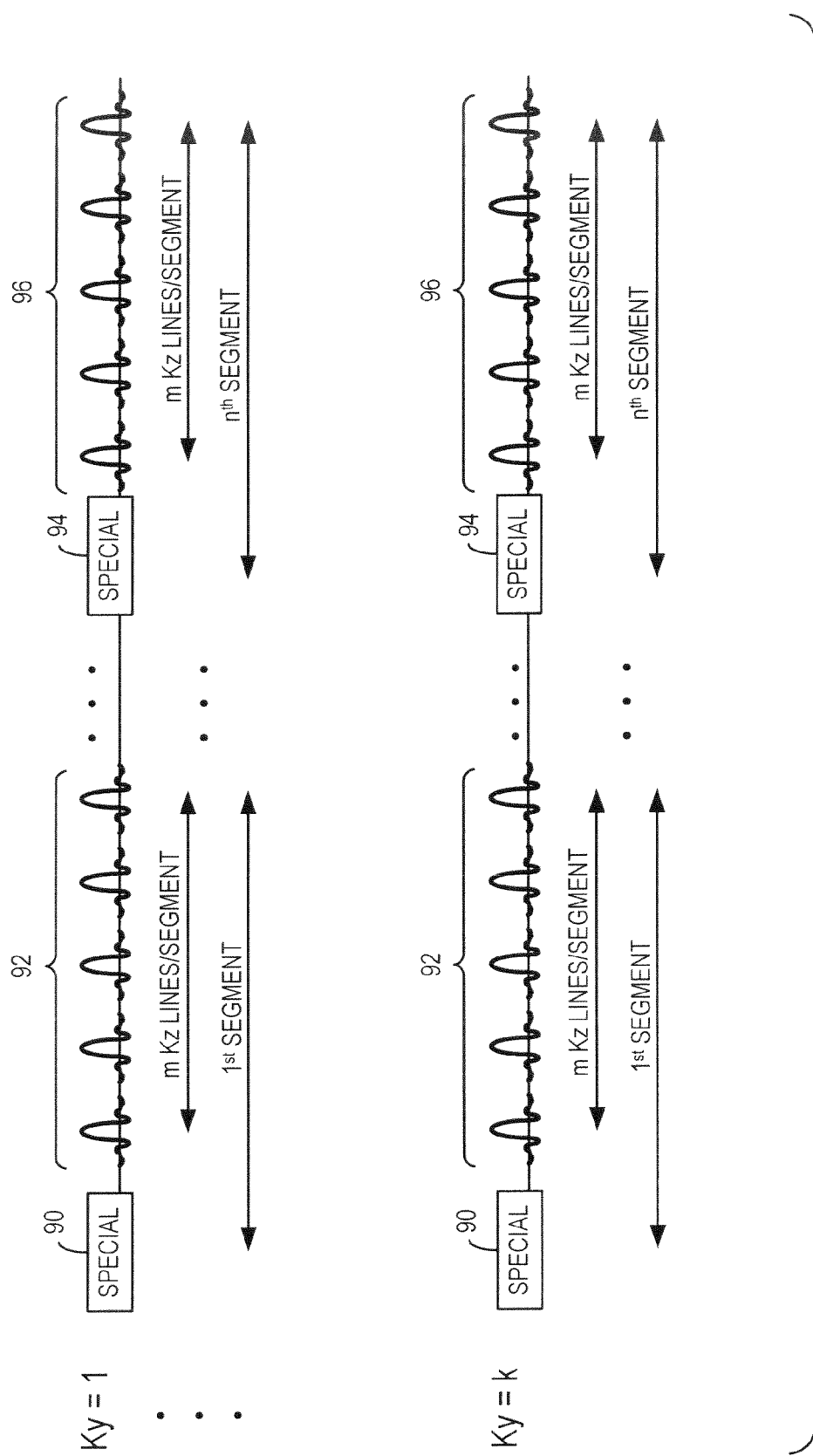

SYSTEM AND METHOD FOR MR DATA ACQUISITION WITH UNIFORM FAT SUPPRESSION

BACKGROUND OF INVENTION

The present invention relates generally to medical imaging and, more particularly, to a system and method for acquiring and reconstructing magnetic resonance (MR) images having uniform fat suppression. Data acquisition is carried out using partial asymmetric acquisitions for dynamic contrast-enhanced imaging having uniform fat suppression.

When a substance such as human tissue is subjected to a uniform magnetic field (polarizing field $B_0$), the individual magnetic moments of the spins in the tissue attempt to align with this polarizing field, but precess about it in random order at their characteristic Larmor frequency. If the substance, or tissue, is subjected to a magnetic field (excitation field $B_1$) which is in the x-y plane and which is near the Larmor frequency, the net aligned moment, or "longitudinal magnetization", $M_z$, may be rotated, or "tipped", into the x-y plane to produce a net transverse magnetic moment $M_t$. A signal is emitted by the excited spins after the excitation signal $B_1$ is terminated and this signal may be received and processed to form an image.

When utilizing these signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received NMR signals are digitized and processed to reconstruct the image using one of many well known reconstruction techniques.

High spatial resolution contrast-enhanced 3D MR imaging techniques have been used clinically for evaluating particular regions-of-interest (ROI) or volumes-of-interest (VOI) to identify abnormalities and pathologies for clinical diagnosis. As is well known, these abnormalities or pathologies are commonly found in lesions in the subject. Moreover, these lesions are commonly found surrounded by fatty tissue. For example, liver metastases or breast lesions are often in close proximity to large concentrations of fat. To acquire MR data with contrast between the lesions and the surrounding fatty tissue, a fat saturation imaging technique is implemented to suppress the fat signal and, ultimately, to enhance the detectability of the lesions in the reconstructed image.

Typically, chemical shift preparation sequences, commonly referred to as "fat suppression," are applied to an imaging space to suppress signals attributable to fat within an imaging subject which may otherwise interfere with identification of a lesion or other pathology. A number of imaging techniques have been developed to enhance contrast between fatty and non-fatty tissues. For example, fat saturation pulses have been shown to improve contrast. However, applying fat saturation pulses can extend the scan time and, therefore, unduly lengthen imaging processes, such as dynamic contrast enhanced imaging studies, as well as decrease patient throughput.

As such, techniques such as that illustrated in FIG. 1 have been developed to suppress fat while reducing scan times. FIG. 1 shows a traditional fast spoiled gradient recalled echo (FSGRE) sequence/data acquisition utilizing a spectrally selective inversion (SPECIAL) pulse 1 to suppress a signal from fat 2. The SPECIAL pulse 1 inverts only the fat magnetization (Mz) without affecting the water proton magnetization. The inverted fat magnetization 3 then recovers over time, across the axis when the fat magnetization or signal is zero 4, to steady state magnetization or full recovery 5. The point where fat magnetization is at zero is referred to as the null point for fat suppression 4. When the fat magnetization is nulled 4, MR data is acquired and used to fill k-space 6 in a centric fashion in the slice direction until all slice encoding Kz lines 7 are acquired. Therefore, for every phase encoding view, only one SPECIAL pulse 1 is applied followed by excitation pulses 8, also called αpulses, which encode all Kz lines 7. This technique is fast, however, it results in non-homogeneous fat suppression, ringing artifacts, and edge enhancement due to non-uniform fat suppression and excessive fat recovery. That is, the Kz lines 7 acquired at or near the null point 4 include little or no data from fat, while data acquired at or near the full fat recovery point 5 include a large influence from unsuppressed fat. Therefore, since data acquisition begins with full fat suppression and continues until fat magnetization has fully recovered 5, non-uniform fat suppression is included across the Kz lines 7, which results in ringing artifacts and edge enhancements in the reconstructed image.

Therefore, while the above-described imaging technique includes fat suppression and does not unduly extend scan times, non-homogeneous fat suppression and ringing may be observed within reconstructed images. That is, while using a spectrally-selective inversion pulse 1 with a centric encoding imaging sequence reduces scan times, it may also result in non-homogeneous fat saturation and is prone to the presence of ringing artifacts in reconstructed images.

It would, therefore, be desirable to have a system and method capable of uniform fat suppression without sacrificing image quality (IQ). Furthermore, such a system and method should be capable of completing an imaging scan within clinically acceptable limits for dynamic contrast enhanced studies.

BRIEF DESCRIPTION OF INVENTION

The present invention provides a system and method of MR imaging that overcomes the aforementioned draw-backs. The present invention includes reconstruction of MR images with uniform or homogeneous fat suppression. An imaging process is performed using partial asymmetric acquisitions in conjunction with zero-filling of k-space for dynamic contrast-enhanced imaging with uniform fat suppression. In this regard, data acquisition is carried out in a relatively short period of time which reduces scan time, reduces the likelihood of subject discomfort and motion-induced artifacts, and increases patient throughput. Further, the present invention yields reconstructed images having fewer artifacts and can be applied for multiple types of pulse sequences/data acquisition using fat suppression, such as a 3D fast Gradient Recalled Echo, spoiled GRASS, Fast Imaging Employing Steady State Acquisition (FIESTA), Time-of-Flight MR Angiography (TOF-MRA), Fast Spin Echo (FSE), Spin Echo (SE), Echo Planar Imaging (EPI), stack spiral, and the like.

In accordance with one aspect of the invention, a method of medical imaging is disclosed that includes the steps of zero-filling at least a first portion of k-space and applying a fat suppression pulse to suppress signals from fat in an ROI. The method includes the steps of acquiring MR data from the ROI prior to full fat recovery and filling at least a second portion of k-space from the MR data.

In accordance with an alternate aspect of the invention, an MRI apparatus is disclosed that includes a magnetic resonance imaging (MRI) system having a plurality of gradient coils positioned about a bore of a magnet to impress a polarizing magnetic field. The MRI apparatus also includes an RF transceiver system and an RF switch controlled by a pulse module to transmit RF signals to an RF coil assembly to acquire MR images. Additionally, the MRI apparatus includes a computer programmed to define an ROI to be sampled for MR data acquisition, select a slice direction, and zero-fill at least a portion of k-space in the slice direction. The computer is also caused to apply a fat suppression pulse to suppress signals from fat in the ROI, acquire MR data from the ROI prior to full fat recovery, and repeatedly apply the fat suppression pulse, and acquire MR data to fill a remainder of k-space with less-than-full-fat-recovery.

In accordance with another aspect of the invention, a computer readable storage medium is disclosed that includes a computer program stored thereon and having instructions which, when executed by a computer, cause the computer to define a slice direction and zero-fill less than an entirety of k-space in the slice direction. The computer is also caused to apply a fat suppression pulse to sup-press fat signals within an ROI, acquire MR data from the ROI prior to full recovery of magnetization of fat within the ROI, and repeat application of the fat suppression pulse and data acquisition to fill a remainder of the entirety of k-space with less-than-full-fat-recovery MR data.

In accordance with yet another aspect of the invention, an MR apparatus is disclosed that includes means for exciting nuclei to precess at a given Lamour frequency when subjected to a substantially uniform magnetic field and means for fastly acquiring 3D MR data with uniform fat suppression during breathhold moments.

Various other features, objects, and advantages of the present invention will be made apparent from the following detailed description and the drawings.

BRIEF DESCRIPTION OF DRAWINGS

The drawings illustrate one preferred embodiment presently contemplated for carrying out the invention.

In the drawings:

FIG. 4 is an illustration of line-by-line k-space sampling with uniform fat suppression for use with the MR imaging system of FIG. 1 and according to the present invention.

DETAILED DESCRIPTION

The present invention is directed to a system and method for acquiring MR data and reconstructing MR images with relatively homogeneous fat suppression, high tissue signal-to-noise ratio (SNR), and contrast-to-noise ratio (CNR). Multiple partial acquisitions are used to acquire MR data to fill a remainder of non-zero filled k-space prior to full fat recovery. Additionally, the system and method allow acquisition of MR data with decreased imaging durations.

Figure 1:
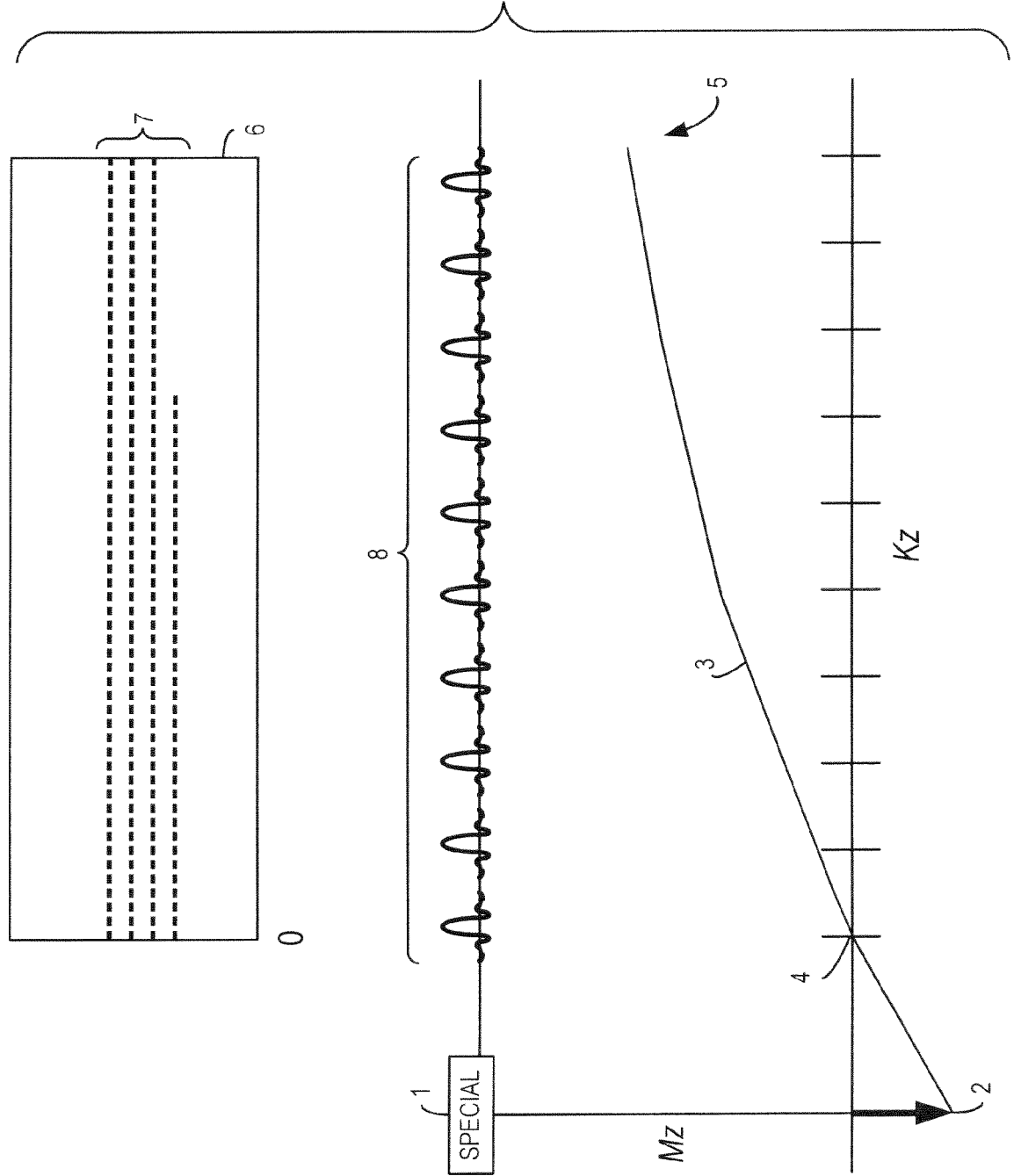
FIG. 1 is an illustration of a known MR data acquisition and k-space filling scheme for fat suppression.
Figure 2:
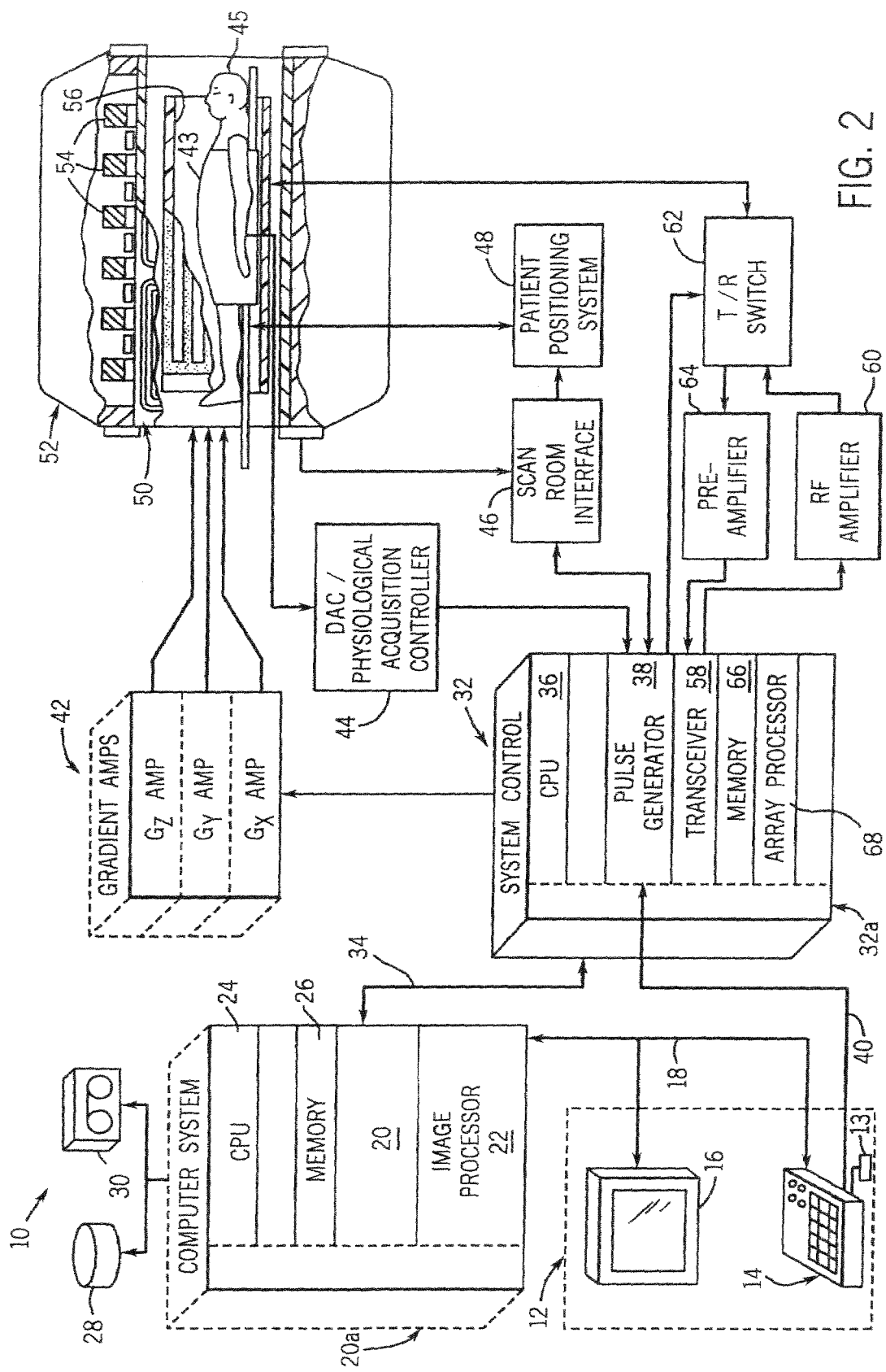
FIG. 2 is a schematic block diagram of a particular MR imaging system for use with the present invention.

Referring to FIG. 2, the major components of an imaging system 10 incorporating the present invention are shown. The invention will be described with reference to a preferred magnetic resonance imaging (MRI) system but other imaging systems are contemplated. Specifically, it is contemplated that the present invention is equally applicable to ultrasound imaging, x-ray imaging, computed tomography imaging, electron beam tomography imaging, positron emission tomography imaging, single photon emission computed tomography imaging, and the like.

Referring to FIG. 2, the operation of the system is controlled from an operator console 12 which includes a keyboard or other input device 13, a control panel 14, and a display screen 16. The console 12 communicates through a link 18 with a separate computer system 20 that enables an operator to control the production and display of images on the display screen 16. The computer system 20 includes a number of modules which communicate with each other through a backplane 20a. These include an image processor module 22, a CPU module 24 and a memory module 26, known in the art as a frame buffer for storing image data arrays. The computer system 20 is linked to disk storage 28 and tape drive 30 for storage of image data and programs, and communicates with a separate system control 32 through a high speed serial link 34. The input device 13 can include a mouse, joystick, keyboard, track ball, touch activated screen, light wand, voice control, or any similar or equivalent input device, and may be used for interactive geometry prescription.

The system control 32 includes a set of modules connected together by a backplane 32a. These include a CPU module 36 and a pulse generator module 38 which connects to the operator console 12 through a serial link 40. It is through link 40 that the system control 32 receives commands from the operator to indicate the scan sequence that is to be performed. The pulse generator module 38 operates the system components to carry out the desired scan sequence and produces data which indicates the timing, strength and shape of the RF pulses produced, and the timing and length of the data acquisition window. The pulse generator module 38 connects to a set of gradient amplifiers 42, to indicate the timing and shape of the gradient pulses that are produced during the scan. The pulse generator module 38 can also receive patient data from a physiological acquisition controller 44 that receives signals from a number of different sensors connected to the patient, such as ECG signals from electrodes attached to the patient.

The pulse generator module 38 connects to a scan room interface circuit 46 which receives signals from various sensors associated with the condition of the patient and the magnet system. It is also through the scan room interface circuit 46 that a patient positioning system 48 receives commands to move the patient to the desired position for the scan. The gradient waveforms produced by the pulse generator module 38 are applied to the gradient amplifier system 42 having $G_x$, $G_y$, and $G_z$ amplifiers. Each gradient amplifier excites a corresponding physical gradient coil in a gradient coil assembly, generally designated as 50, to produce the magnetic field gradients used for spatially encoding acquired signals. The gradient coil assembly 50 forms part of a magnet assembly 52 which includes a polarizing magnet 54 and a whole-body RF coil 56. A transceiver module 58 in the system control 32 produces pulses which are amplified by an RF amplifier 60 and coupled to the RF coil 56 by a transmit/receive switch 62. The resulting signals emitted by the excited nuclei in the patient may be sensed by the same RF coil 56 and coupled through the transmit/receive switch 62 to a preamplifier 64. The amplified MR signals are demodulated, filtered, and digitized in the receiver section of the transceiver 58. The transmit/receive switch 62 is controlled by a signal from the pulse generator module 38 to electrically connect the RF amplifier 60 to the coil 56 during the transmit mode and to connect the preamplifier 64 to the coil 56 during the receive mode. The transmit/receive switch 62 can also enable a separate RF coil (for example, a surface coil) to be used in either the transmit or receive mode.

The MR signals picked up by the RF coil 56 are digitized by the transceiver module 58 and transferred to a memory module 66 in the system control 32. A scan is complete when an array of raw k-space data has been acquired in the memory module 66. This raw k-space data is rear-ranged into separate k-space data arrays for each image to be reconstructed, and each of these is input to an array processor 68 which operates to Fourier transform the data into an array of image data. This image data is conveyed through the serial link 34 to the computer system 20 where it is stored in memory, such as disk storage 28. In response to commands received from the operator con-sole 12, this image data may be archived in long term storage, such as on the tape drive 30, or it may be further processed by the image processor 22 and conveyed to the operator console 12 and presented on the display 16.

Figure 3:
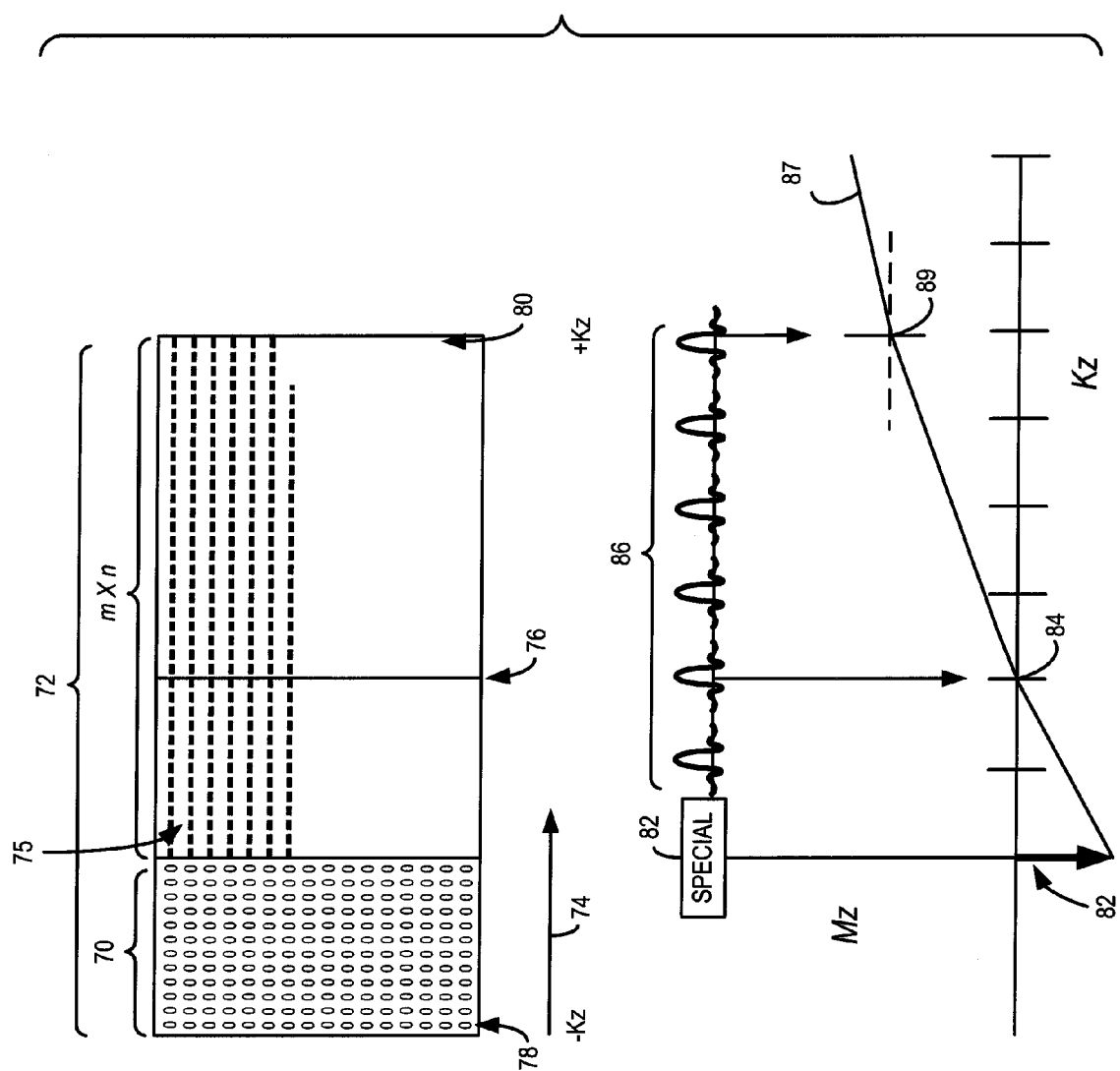
FIG. 3 is a graphical illustration of an imaging technique and k-space filling scheme with uniform fat suppression for use with the MR imaging system of FIG. 1.

FIGS. 3 and 4 illustrate an MR data acquisition and k-space filling scheme for subsequent image reconstruction of a region-of-interest (ROI) or volume-of-interest (VOI) with homogeneous fat suppression and decreased data acquisition times. FIG. 3 graphically illustrates an imaging technique with asymmetric, partial zero-filling 70 of k-space 72 in some percentage of slice encoding that follows partial Fourier theory. While zerofilling 70 of k-space 72 is shown as performed in the slice encoding direction 74, it is contemplated that zero-filling of k-space 72 may occur from the periphery 75 of k-space 72 to the center 76 of k-space 72 to fill a desired percentage of the slice encoding lines. For example, zero-filling 70 may be carried out from the first Kz line 78 toward the center of k-space 76, or from the center of k-space 76 to the last Kz line 80. This partial zero-filling technique reduces the scan time proportionally to the fraction of the zero-filling to the total number of Kz lines.

After the zero-filling, a SPECIAL inversion pulse 82 with a 100 degree fat suppression pulse to magnetize fat within the ROI or VOI is applied based on the relaxation time of fat to its null point 84. Following the application of a SPECIAL inversion pulse 82, $\alpha$ excitation pulses 86 are applied to encode only m Kz lines that are arranged sequentially in the k-space. That is, less than all Kz lines are filled after the SPECIAL pulse. Therefore, in this regard, only m lines after the application of inversion pulse 82 are filled so that the data acquisition is completed within a certain limit of the fat magnetization recovery and thereby avoids data acquisition as fat magnetization reaches a fully recovered state 87. Specifically, zero-filling of k-space 72 is carried out such that all the non-zero filled phase encoding steps of k-space 72 are sampled before fat magnetization passes a threshold point 89. As will be described with respect to FIG. 4, these steps are repeated for a number of segments until all the non-zero filled Kz lines are filled.

The flip angle of the SPECIAL inversion pulse 82 is automatically adjusted such that magnetization of fat within the ROI or VOI is at or near a null point at the filling of the center of k-space 76. In one embodiment of the invention, the first Kz lines acquired after the SPECIAL inversion pulse (at or near 100 degrees) are placed very close to the center of k-space for the ROI or VOI 78, which provides good SNR and CNR. As such, in contrast to known fat suppression techniques, data is acquired before fat magnetization reaches its null point 84.

Furthermore, it should be noted that the non-zero filled portions of k-space 72 can be filled in a reverse sequential manner. That is, data may be acquired for the $+k_z$ periphery 80 of k-space toward the zero-filled section 70 of k-space 72 (e.g., acquire data sequentially from right to left in the illustration of k-space of FIG. 3). Using a reverse sequential k-space filling scheme, the SPECIAL inversion flip angle may be slightly higher than used with the sequential k-space filling scheme in order to fill the center of k-space at or near the null point of fat. Both the sequential and reverse sequential ordering schemes result in a smooth k-space trajectory that reduces artifacts that are usually found with centric encoding extending through excessive fat recovery.

It should be noted that without the partial zero-filling 70 of FIG. 3, the segmented acquisition would result in longer scan time due to the multiple SPECIAL inversion pulses. However, the use of partial zero-filling 70 in the segmented fashion results in reduced scan times over conventional SPECIAL methods in addition to the benefits of providing homogeneous fat suppression. Therefore, in contrast to conventional partial-zero-filling in the view direction, which results in low in-plane spatial resolution and artifacts, the present invention includes partial-zero-filling 70 in the slice direction. As such, high in-plane spatial resolution is maintained with a reduction of scan time.

Once partial zero-filling, as described with respect to FIG. 3, is complete, segmented data acquisition is performed. FIG. 4 illustrates segmented acquisition in the slice direction using a SPECIAL pulse applied with a 3D FGRE sequence. Specifically, slice-encoding is used to fill the non-zero-filled k-space in a segmented fashion. That is, for every phase encoding view (Ky=1 line to Ky=k line), a first SPECIAL pulse 90 is applied followed by a set number of a pulses 92 to acquire only m Kz lines before applying a subsequent SPECIAL pulse 94 and $\alpha$ pulses 92. This technique is repeated n times (segments), which may be in an interleaved manner, until all Kz lines, from the $1^{st}$ to the $n^{th}$ k-space segment, are filled. That is, for each Ky line, m X n data may be filled. Therefore, the above-described imaging technique combines partial zero-filling in the slice direction and segmented sequential acquisition with spectrally selective inversion recovery pulses. This technique results in homogeneous fat suppression as well as reduced ringing and edge enhancement in reconstructed images.

The number of lines per segments (m) and the number of segments (n) may be selected and optimized based on clinical applications in the body. For example, it is contemplated that the above-described technique may be specifically tailored for breathhold and non-breathhold imaging processes as well as anatomic-specific imaging processes of various regions of the body such as liver, pelvic, and breast imaging.

For example, for breathholding applications, such as liver imaging, the maximum number of lines per segment may be set to approximately eighteen (m=18). Additionally, the number of segments may vary based on the number of slices prescribed. For example, in a liver scan with a prescription of 48 slices, the number of segments would be two (n=2) to suppress signals from fat. Additionally, in the context of a breast scan, a maximum of ten lines per segment (m=10) may be used due to the fact that breasts are typically composed of mostly fatty tissue. With a breast scan with a prescription of 54 slices, the number of segments would be four (n=4) to suppress the signal from fat.

Figure 6:
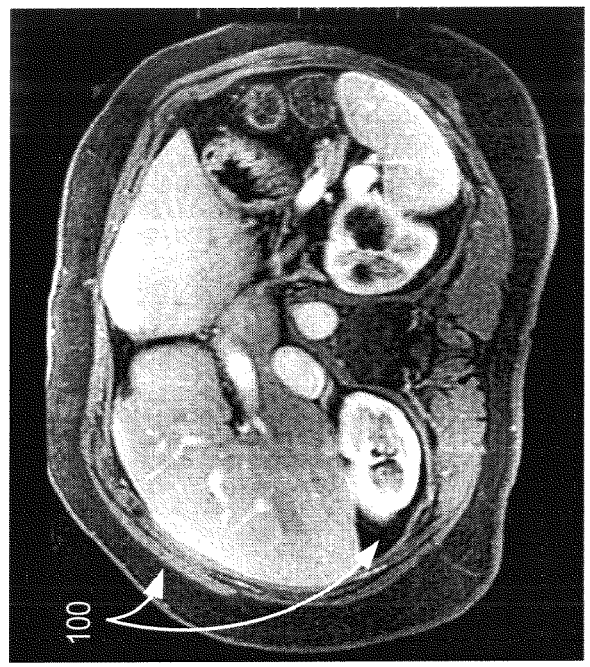
FIG. 6 is a liver image reconstructed from MR data acquired according to the technique of FIGS. 3 and 4.
Figure 5:
FIG. 5 is a liver image reconstructed from MR data acquired according to a conventional fat suppression technique.

FIGS. 5 and 6 show liver images reconstructed from MR data acquired according to a conventional fat suppression technique and the above-described technique having uniform fat suppression, respectively. As shown in FIG. 5, the image reconstructed from MR data acquired using conventional SPECIAL fat suppression, which includes data acquired at full fat recovery, shows non-uniform fat suppression, ringing, and edge enhancements. However, referring to FIG. 6, as illustrated by the uniformly darkened fatty areas 100, fat is homogenously suppressed while maintaining high image quality (IQ).

It is contemplated that the segmented acquisition may be optimized based on clinical applications. For example, only a few number of segments are needed for liver application because of its breathholding requirement. On the other hand, for breast imaging that does not require breathholding, the number of segments is played out more often than during liver imaging. A number of segments may also be played out to suppress the breast tissue that is mostly composed of fat substances. Image quality is high and little or no ringing artifacts or edge enhancements are present within reconstructed images.

The above-described technique allows homogeneous fat suppression with high tissue SNR and CNR that can be achieved with shorter acquisition time than the conventional techniques utilizing SPECIAL pulses. The technique provides high SNR and CNR due to the sequential encoding scheme that fills the center of k-space at or near the null point of fat. Additionally, the present invention achieves relatively uniform fat suppression with data acquisition at high bandwidth and high resolution matrices for large volume coverage. Further, the above-described technique includes similar benefits as centric encoding schemes utilizing SPECIAL but with increased fat suppression and reduced scan times. Specifically, the imaging technique has a smooth k-space trajectory that starts at or near the center of k-space for increased fat saturation and reduced artifacts. Moreover, while the present invention is particularly well-suited for 3D data acquisition, the present invention may also be applicable with 2D acquisitions.

The above-described imaging technique combines partial zero-filling in the slice direction and segmented sequential acquisition or segmented reverse sequential acquisition with spectrally selective inversion recovery pulses. The technique is robust and can be applied with fast gradient echo sequences where data is acquired with high bandwidth, high spatial resolution for large volume coverage. It is contemplated that the present invention may be utilized with a wide variety of imaging processes. For example, it is contemplated that the technique may be utilized with gradient echo (GRE), SE, FSE, GRE, FGRE, EPI, SPCR, FIESTA, TOF-MRA, contrast-enhanced MRA with fluoroscopic triggering, stack spiral readout, and the like.

Furthermore, the technique provides uniform fat suppression within a single breathhold period or free breathing. Additionally, the technique is applicable for most body applications including liver imaging, breast acquisition, contrast-enhanced angiography with fluoroscopic triggering, or multi station imaging. The technique reduces or eliminates ringing and edge enhancement caused by excessive fat recovery.

Therefore, the present invention includes a method of medical imaging that includes the steps of zero-filling at least a first portion of k-space and applying a fat suppression pulse to suppress signals from fat in an ROI. The method includes the steps of acquiring MR data from the ROI prior to full fat recovery and filling at least a second portion of k-space from the MR data.

In an alternate embodiment of the invention, an MRI apparatus includes a magnetic resonance imaging (MRI) sys-tem having a plurality of gradient coils positioned about a bore of a magnet to impress a polarizing magnetic field. The MRI apparatus also includes an RF transceiver system and an RF switch controlled by a pulse module to transmit RF signals to an RF coil assembly to acquire MR images. Additionally, the MRI apparatus includes a computer programmed to define an ROI to be sampled for MR data acquisition, select a slice direction, and zero-fill at least a portion of k-space in the slice direction. The computer is also caused to apply a fat suppression pulse to suppress signals from fat in the ROI, acquire MR data from the ROI prior to full fat recovery, and repeatedly apply the fat suppression pulse, and acquire MR data to fill a remainder of k-space with less-than-full-fat-recovery.

The present invention may also be embodied in a computer readable storage medium that includes a computer program stored thereon and instructions which, when executed by a computer, cause the computer to define a slice direction and zero-fill less than an entirety of k-space in the slice direction. The computer is also caused to apply a fat suppression pulse to suppress fat signals within an ROI, acquire MR data from the ROI prior to full recovery of magnetization of fat within the ROI, and re-peat application of the fat suppression pulse and data acquisition to fill a remainder of the entirety of k-space with less-than-full-fat-recovery MR data.

In accordance with yet another embodiment of the invention, an MR apparatus is disclosed that includes means for exciting nuclei to precess at a given Lamour frequency when subjected to a substantially uniform magnetic field and means for fastly acquiring 3D MR data with uniform fat suppression during breathhold moments.

The present invention has been described in terms of the preferred embodiment, and it is recognized that equivalents, alternatives, and modifications, aside from those expressly stated, are possible and within the scope of the appending claims.

What is claimed is:

1. A method of medical imaging comprising the steps of:
   zero-filling at least a first portion of k-space;
   applying a fat suppression pulse to suppress signals from fat in an ROI;
   acquiring MR data from the ROI prior to full fat recovery with a 3D fast gradient echo sequence (FGRE);
   filling at least a second portion of k-space from the MR data; and
   reconstructing a uniformly fat-suppressed medical image from the MR data having fat magnetization suppressed below a uniform threshold above which the fat magnetization is deemed to have fully recovered.

2. The method of claim 1 wherein the step of acquiring MR data includes segmenting data acquisitions into a number of imaging segments for each phase encoding view, and acquiring multiple slice encoding lines per imaging segment, and further comprising the steps of repeating application of the fat suppression pulse for MR data acquisition for each imaging segment.

3. The method of claim 2 further comprising the step of filling each phase encoding view of k-space with fat-suppressed MR data.

4. The method of claim 3 wherein the step of filling includes sampling MR signals from the ROI with a segmented sequential encoding order having a k-space trajectory starting at or near a center of k-space to a periphery of k-space.

5. The method of claim 4 further comprising the step of determining a flip angle for the fat suppression pulse such that magnetization of fat within the ROI is at or near a null point at the filling of the center of k-space.

6. The method of claim 3 wherein the step of filling includes sampling MR signals from the ROI with a reverse segmented sequential encoding order having a k-space trajectory from a periphery of k-space to at or near a center of k-space.

7. The method of claim 6 further comprising the step of determining a flip angle for the fat suppression pulse such that magnetization of fat within the ROI is at or near a null point at the filling of the center of k-space.

8. The method of claim 1 wherein the step of zero-filling includes zero-filling in a slice direction.

9. The method of claim 1 wherein the fat suppression pulse includes a spectrally-selective inversion recovery pulse.

10. The method of claim 1 further comprising the step of acquiring the MR data during at least one of a breathhold and a non-breathhold moment.

11. The method of claim 1 further comprising the step of sequentially sampling the ROI and sequentially filling the non-zero filled portions of k-space.

12. The method of claim 1 further comprising the step of defining a 3D volume of interest (VOI), and wherein the step of acquiring MR data includes the acquisition of 3D data from the VOI.

13. The method of claim 1 wherein the step of acquiring MR data includes sampling MR signals from an excited region surrounding one of a liver or breast region of a medical patient.

14. The method of claim 1 further comprising the step of reconstructing a magnetic resonance angiography (MRA) image from the MR data.

15. A magnetic resonance imaging (MRI) apparatus to reconstruct MR images with substantially uniform fat suppression comprising:
   an MRI system having a plurality of gradient coils positioned about the bore of a magnet to impress a polarizing magnet field and an RF transceiver system and an RF switch controlled by a pulse module to transmit RF signals to an RF coil assembly to acquire MR images; and
   a computer programmed to:
      define an ROI to be sampled for MR data acquisition;
      select a slice direction;
      zero fill at least a portion of k-space in the slice direction;
      apply a fat suppression pulse to suppress signals from fat in the ROI;
      acquire MR data from the ROI prior to full fat recovery; and
      repeatedly apply the fat suppression pulse and acquire MR data to fill a remainder of k-space with less-than-full-fat-recovery.

16. The MRI apparatus of claim 15 wherein the computer is further programmed to acquire the MR data during at least one of a breathhold and a non-breathhold moment.

17. The MRI apparatus of claim 15 wherein the computer is further programmed to sequentially fill the non-zero filled portions of k-space.

18. The MRI apparatus of claim 15 wherein the computer is further programmed to reconstruct a fully fat-suppressed medical image from the MR data.

19. The MRI apparatus of claim 15 wherein the fat suppression pulse includes a spectrally-selective inversion recovery pulse.

20. A computer readable storage medium having a computer program stored thereon and representing a set of instructions that when executed by a computer causes the computer to:
   define a slice direction;
   zero fill less than an entirety of k-space in the slice direction;
   apply a fat suppression pulse to suppress fat signals within an ROI;
   acquire MR data from the ROI prior to full recovery of magnetization of fat within the ROI; and
   repeat application of the fat suppression pulse and data acquisition to fill a remainder of the entirety of k-space with less-than-full-fat-recovery MR data.

21. The computer program of claim 20 wherein the computer is further caused to acquire MR data with one of segmented sequential encoding, reverse segmented sequential encoding, and centric encoding of k-space.

22. The computer program of claim 20 wherein the computer is further caused to automatically determine a flip angle of the fat suppression pulse such that fat is at or near its null point at the filling of a center of k-space.

23. The computer program of claim 22 wherein the flip angle is determined as at least a function of one of a segmented sequential encoding scheme and a reverse sequential encoding scheme.

24. The computer program of claim 23 wherein the flip angle is set to 100 degrees for the segmented sequential encoding scheme and set to more than 100 degrees for the reverse sequential encoding scheme.

25. An MR apparatus comprising:
   means for exciting nuclei to precess at a given Larmor frequency when subjected to a substantially uniform magnetic field; and
   means for fastly acquiring 3D MR data only when fat magnetization is suppressed below a full-recovery threshold during breathhold moments.

* * * * *